July 5, 1966 H. C. SWIM ETAL Plant Pat. 2,648
ROSE PLANT
Filed July 15, 1965
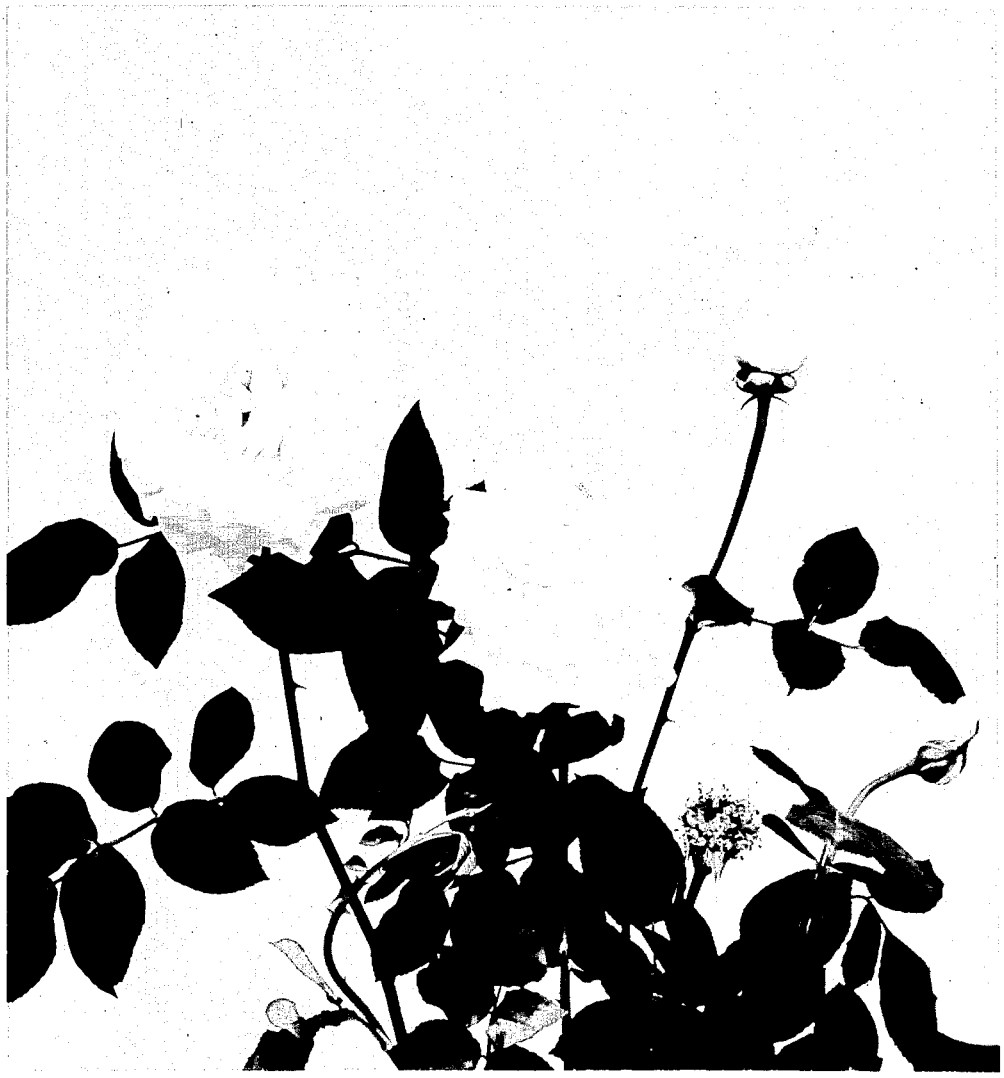
Inventors.
H. C. Swim
O. L. Weeks
By: Robb & Robb
Attorneys.

United States Patent Office

Plant Pat. 2,648
Patented July 5, 1966

2,648
ROSE PLANT

Herbert C. Swim, Ontario, and O. L. Weeks, Chino, Calif., assignors to Swim and Weeks, Chino, Calif., a copartnership Filed July 15, 1965, Ser. No. 472,376
1 Claim. (Cl. Plt.—14)

The present invention relates to a new and distinct variety of rose plant of the hybrid tea class, which was originated by us by crossing the variety "Mount Shasta" (Plant Patent No. 2,132) with the variety "White Butterfly" (Plant Patent No. 1,337).

As the result of this breeding, we have produced a new rose variety having the following unique combination of characteristics which are outstanding therein and which distinguish it from its parents, as well as from all other varieties of which we are aware:

(1) A very vigorous and bushy, but tall, habit of growth;

(2) Leaves having a tough, leathery substance and better than average resistance to mildew as compared with other white hybrid tea rose varieties suitable for greenhouse production of commercial cut flowers;

(3) Relatively long flower stems;

(4) A flower size ranging from medium to large;

(5) Good flower petalage;

(6) A high-centered flower form at the opening stage and relatively long retention of this form after opening;

(7) A distinctive and attractive flower color ranging from white to near white; and (8) Relatively long-keeping qualities of the flowers as cut flowers.

In comparison with its seed parent "Mount Shasta," the new variety is much branched as distinguished from the moderately branched habit of this parent variety, and the contrast is especially applicable to the base of the plant; the new variety rarely produces more than a single flower to a stem, whereas the flowers of the parent variety are borne in groups of two or three to a stem; the flowers of the new variety have substantially greater petalage, ranging between 60 to 80 petals, whereas those of the parent variety have from 20 to 26 petals; and the flower filaments of the new variety are whitish-yellow green in color as distinguished from the reddish filaments of the flowers of the parent variety.

As compared with its pollen parent "White Butterfly," the new variety has a tall-growing habit instead of the low-growing habit of this parent; the branches and stems of the new variety are unusually long instead of being of moderate length like the branches of the parent variety; the flowers have many more petals, usually ranging between 60 to 80 petals, while the flowers of the parent variety usually have between 22 and 24 petals and rarely more than 35 petals; and the flowers of the new variety are high-centered instead of being characteristically low-centered like the flowers of this parent.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Tall; bush; greenhouse; seedling; for cut flowers.
Class: Hybrid tea.
Breeding: Seedling.
*Seed parent.*—"Mount Shasta."
*Pollen parent.*—"White Butterfly."
Propagation: Holds its distinguishing characteristics through succeeding propagations by budding.

*Flower*

Locality where grown and observed: Chino, California.
Flowers borne: Singly to stem; on long stems of normal strength.
Quantity of bloom: Abundant, in greenhouse.
Continuity: More or less continuous.
Fragrance: From moderate to strong. Nature—tea.
Bud:
*Peduncle.*—From medium length to long; medium caliper; slightly bending at times; smooth, except for numerous microscopic short hairs. Color—medium yellowish-green.
*Before calyx breaks.*—Size—large. Form—short pointed; with a conspicuous neck; without foliaceous appendages on the surface of the bud; usually without foliaceous parts extending beyond the tip of the bud, or more or less vestigial, if any. Color—between Strong Yellow Green, Plate 7.5GY 6/8 and Moderate Yellow Green, Plate 7.5GY 5/7.
*As calyx breaks.*—Color—greenish-white.
*As first petal opens.*—Size—from medium to large for its class. Form—from long-pointed to urn-shaped. Color: Outside—white or near white, with slight greenish influence on lower portion of petal and especially on midrib; inside—white over most of petal, with greenish midrib on lower half of petal and some yellowish-green shading in area immediately above point of attachment.
*Opening.*—Opens up well.
Bloom:
*Size (when fully open).*—From medium to large for its class; from 4 inches to 4½ inches.
*Petalage.*—From double to very double; from 60 to 80 petals, plus 8 to 10 petaloids; arranged regularly.
*Form.*—High-centered at first and remaining high-centered; petals being flat at first but later becoming loosely rolled outward at maturity.
Petals:
*Texture.*—Thick for color class and horticultural class combination; leathery.
*Appearance.*—Inside—satiny. Outside—satiny.
*Shape.*—Outside—obovate and more or less scalloped, with apex acute and with several notches of variable depth and at variable positions on the margin, often with 1 or 2 guard petals on the outside which are particularly irregularly notched and have an irregular general outline. Intermediate—obovate and occasionally scalloped, with apex acute and rather blunt. Inside—slenderly obovate and from wrinkled to scalloped irregularly with apex bluntly acute.

This description of a newly opened flower was made from a rose grown in a greenhouse during the month of May at Chino, California.

*Color.*—Outer petal: Outside surface—white or near white over most of petal, with midrib on lower half slightly yellow-green and being more discenible near base, with very faint yellow influence discernible on lower half; inside surface—white or near white, with faint greenish cast which becomes more apparent on lower half, and with midrib being light greenish-yellow on lower half of somewhat deeper intensity. Intermediate petal: Outside surface—very near white, except near point of attachment where there is a faint yellowish-green influence; inside surface—white on upper portion, with lower half faintly tinted with yellowish-green and being most discernible at point of attachment. Inner petal: Outside surface—white, but with faint yellowish-green influence over lower half of petal; inside surface—near white, especially on outer portions but with yellowish-green influence faintly appearing over lower half of petal.

This description was made from a rose that was open for three days in a greenhouse during the month of May at Chino, California.

*Color.*—Outer petal: Outside surface—near white, but with very slight yellowish appearance on lower half of petal, especially on midrib and at point of attachment; inside surface—white or near white, except for midrib which has a very faint greenish cast on lower half and that portion of petal near point of attachment which is very faintly yellowish-green. Inner petal: Outside surface—white, except for small area around point of attachment which is near Brilliant Greenish-Yellow, Plate 7.5Y 9/8; inside surface—white over upper portion of petal, but lower portion being influenced by faint yellow which becomes near Brilliant Greenish-Yellow, Plate 7.5Y 9/8 near and at point of attachment.

*General color effect.*—Newly opened flower—white on outer part of flower, with center only mildly influenced by rather faint greenish-yellow cast. Three days open—white, with only faint creamy yellow influence in center of bloom.

*Behavior.*—Drop off cleanly, but petaloids persist.

*Flower longevity.*—Cut roses grown in greenhouse and kept at living room temperatures—5 days in May.

*Reproductive organs*

Stamens: Medium quantity; arranged irregularly about pistils and mixed with petaloids.

Filaments: From medium length to long; most with anthers. Color—whitish-yellow green.

Anthers: Small for class; open at various times. Color—yellow, with reddish valves.

Pollen: Moderate quantity. Color—from gold to yellow.

Pistils: Many.

Styles: Somewhat uneven; from short to medium length; medium caliper; more or less bunched.

Stigma: Color—from white to pinkish-white.

Ovaries: Most protruding from calyx.

Hips: Long; flat at top; with conspicuous neck; smooth, but with short microscopic hairs; walls thick and fleshy. Color—yellow at maturity.

Sepals: Permanent; straight; from spear-shaped to curled.

Seeds: Many; medium size.

*Plant*

Foliage:

*Leaves.*—Compound of 3 to 5 leaflets; normal quantity; medium size; moderately heavy; leathery.

*Leaflets.*—Shape—from oval to elliptical. Apex—from acute to acuminate. Base—from round to acute. Margin—simply serrate, but often entire or nearly so at base.

*Color.*—Mature: Upper surface—dark green; under surface—grey green. Young: Upper surface—yellow-green, with midrib and venations of reddish-purple; under surface—grey green, with midrib and veins shaded with reddish-purple in varying intensities.

*Rachis (the supporting stem of the compound leaf).*—Medium weight. Upper side—grooved; sparsely glandular. Under side—smooth, except for 1 or 2 prickles.

*Stipules.*—Moderately short; very narrow; with short points recurved toward the stem.

*Disease resistance.*—Above average resistance to powdery mildew, as determined by comparison with other white hybrid tea varieties grown in greenhouse under comparable cultural conditions at Chino, California.

Growth:

*Habit.*—Tall; bushy; upright; much-branched.

*Growth.*—Very vigorous.

*Canes.*—Medium caliper.

*Main stems.*—Color—yellow green. Large prickles—from short to medium length; straight; with short, broad base; color—brown. Small prickles—few; color—brown. Hairs—none.

*Branches.*—Color—grey green. Large prickles—few; from short to medium length; straight; with short broad base; color—brown. Small prickles—few; color—brown. Hairs—none.

*New shoots.*—Color—green, with reddish overlay. Large prickles—several; medium long; straight; with short, broad base; color—green, with some reddish-purple at base. Small prickles—few; color—green, with reddish-purple shading at base. Hairs—none.

We claim:

A new and distinct variety of rose plant of the hybrid tea class, substantially as herein shown and described, characterized particularly as to novelty by the unique combination of a very vigorous and bushy, but tall, habit of growth, leaves having a tough, leathery substance and better than average resistance to mildew as compared with other white hybrid tea rose varieties suitable for greenhouse production of commercial cut flowers, relatively long flower stems, a flower size ranging from medium to large, good flower petalage, a high-centered flower form at the opening stage and relatively long retention of this form after opening, a distinctive and attractive flower color ranging from white to near white, and relatively long-keeping qualities of the flowers as cut flowers.

No references cited.

ANTONIO F. GUIDA, *Acting Primary Examiner.*

R. E. BAGWILL, *Assistant Examiner.*